United States Patent [19]
Kamen

[11] Patent Number: 5,195,986
[45] Date of Patent: Mar. 23, 1993

[54] INTEGRAL INTRAVENOUS FLUID DELIVERY DEVICE

[75] Inventor: Dean L. Kamen, Bedford, N.H.

[73] Assignee: DEKA Products Limited Partnership, Manchester, N.H.

[21] Appl. No.: 908,524

[22] Filed: Jun. 29, 1992

Related U.S. Application Data

[63] Continuation of Ser. No. 614,806, Nov. 19, 1990, abandoned, which is a continuation-in-part of Ser. No. 523,801, May 15, 1990, Pat. No. 5,088,515, and a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and a continuation-in-part of Ser. No. 836,023, Mar. 4, 1986, Pat. No. 4,778,451.

[51] Int. Cl.$^5$ .......................... A61M 5/00; A61M 5/14
[52] U.S. Cl. ....................... 604/251; 604/247; 604/132; 604/153; 128/DIG. 13
[58] Field of Search ........ 604/127, 131, 132, 251–255, 604/246, 247, 150–153; 128/DIG. 12, DIG. 13

[56] References Cited

U.S. PATENT DOCUMENTS

| | | | |
|---|---|---|---|
| 3,204,632 | 9/1965 | Hofstra | 128/214 |
| 4,055,176 | 10/1977 | Lundquist | 128/214 |
| 4,116,646 | 9/1978 | Edwards | 604/252 |
| 4,300,552 | 11/1981 | Cannon | 128/214 |
| 4,326,957 | 4/1982 | Rosenberg | 210/436 |
| 4,430,074 | 2/1984 | Mooring | 604/49 |
| 4,479,760 | 10/1984 | Bilstad et al. | 417/395 |
| 4,515,588 | 5/1985 | Amendolia | 604/247 |
| 4,519,792 | 5/1985 | Dawe | 604/123 |
| 4,710,166 | 12/1987 | Thompson et al. | 604/65 |
| 4,804,360 | 2/1989 | Kamen | 604/250 |
| 4,808,161 | 2/1989 | Kamen | 604/67 |
| 4,838,856 | 6/1989 | Mulreany et al. | |
| 4,842,584 | 6/1989 | Pastrone | 604/153 |
| 4,846,636 | 7/1989 | Danby et al. | 604/153 |
| 4,941,875 | 7/2990 | Brennan | 604/81 |

FOREIGN PATENT DOCUMENTS

990583 4/1965 United Kingdom .
90/13795 11/1990 World Int. Prop. O. .

Primary Examiner—John D. Yasko
Assistant Examiner—Chalin Smith
Attorney, Agent, or Firm—Bromberg & Sunstein

[57] ABSTRACT

A compact, integrated intravenous fluid delivery device. The invention may be used between an intravenous fluid source and an intravenous fluid line. In this embodiment, the invention includes a housing, through which a fluid passageway is disposed. The fluid passageway passes through a spike, which is used for connecting the housing to the fluid source. The passageway also passes through a rigid drip chamber and a priming element that may be repeatedly compressed in order to urge fluid from the source into the drip chamber and through the intravenous fluid line. The priming element includes a rigid base portion and a membrane. The spike, drip chamber and the base of the priming element all form an integral piece of rigid material. This embodiment may further include a valve chamber disposed in the housing, such that the fluid passageway enters and exits the chamber through two mouths. A valve membrane is attached to the housing and covers the valve chamber, so that the membrane may be urged to cover at least one of the two mouths.

14 Claims, 8 Drawing Sheets

INTEGRAL INTRAVENOUS FLUID DELIVERY DEVICE

This is a continuation of application Ser. No. 614,806 filed Nov. 19, 1990, which is a continuation-in-part of applications Ser. No. 523,801, filed May 15,1990, issued as U.S. Pat. No. 5,085,515 and Ser. No. 345,387 filed May 1, 1989, issued as U.S. Pat. No. 4,976,162 which is a continuation-in-part of application Ser. No. 092,481 filed Sept. 3, 1987, issued as Pat. No. 4,826,482, which is a continuation-in-part of applications Ser. No. 022,167 filed Mar. 5, 1987, issued as U.S. Pat. No. 4,808,161, and Ser. No. 836,023 filed on Mar. 4, 1986, issued as U.S. Pat. No. 4,778,451. These related applications are hereby incorporated herein by reference.

DESCRIPTION

1. Technical Field

The invention relates generally to intravenous fluid delivery systems, and more particularly to integrated fluid delivery systems.

2. Background Art

Figure 1:
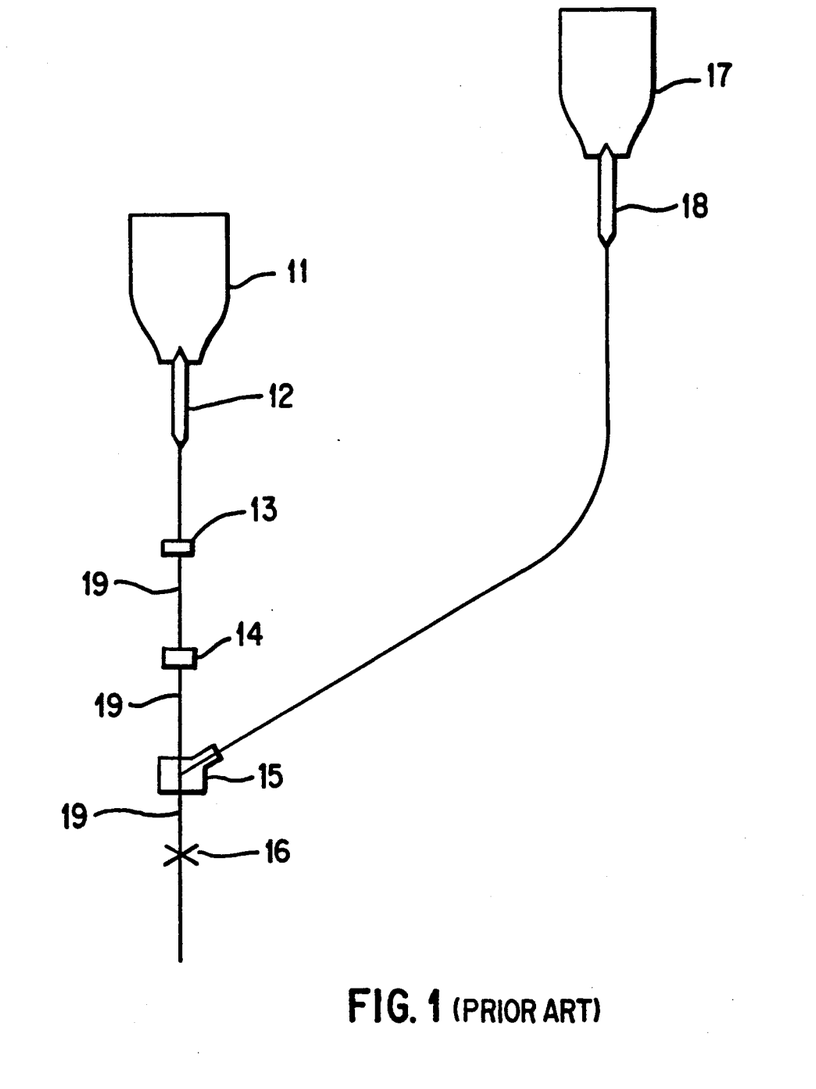
FIG. 1 shows a prior art fluid delivery system.

Integrated spike/drip chamber structures are well known. In these known systems, the spike is inserted into the intravenous fluid reservoir, and the drip chamber is connected to a tube, through which the intravenous fluid flows to the patient. Typically, a puncture site is provided along this tubing, so that a second source of intravenous fluid (containing, for example, medication) can be provided to the patient. If it is desired to provide the second source of intravenous fluid to the patient in lieu of the first until the second source is exhausted, the arrangement shown in FIG. 1 may be used. A duckbill (one-way way) valve 14 is provided in the tubing above the puncture site 15 and below the drip chamber 12 for the first source of intravenous fluid 11, and the second source 17 is hung at a higher level than the first 11. With this arrangement, the higher head pressure of the second source 17 forces the duckbill valve 14 closed so that only the second fluid flows to the patient until the second fluid is exhausted. At this point the duckbill valve 14 opens and allows the first fluid to flow to the patient. Such an arrangement allows one to keep the vein open with intravenous fluid until it is desired to administer the medication, and it allows the continuation of intravenous fluid flow to the vein immediately after the medication is depleted. In order to control the flow rate of the intravenous fluid, a clamp 16 may be placed below the puncture site 15. Typically, such clamps are simply placed on the tubing 19 and control the flow by squeezing the tubing 19. Placing the clamp 15 between the puncture site 15 and the drip chamber 12 may cause problems in the administration of intravenous fluid. In these systems, the various components (e.g., the duckbill valve 14, the filter 13 and the puncture site 15) are each separately disposed in the intravenous tubing 19, such that both ends of each component must be cemented to the tubing 19.

It is known to have an integrated spike/valve/drip chamber structure. U.S. Pat. No. 4,804,360, issued to Kamen, is directed towards a valve disposed in a spike.

SUMMARY OF THE INVENTION

The present invention provides for a compact, integrated intravenous fluid delivery device. In one embodiment, the invention is used with an intravenous fluid source and an intravenous fluid line. In this embodiment, the invention includes a housing, through which a fluid passageway is disposed. The fluid passageway passes through a spike, which is used for connecting the rigid housing to the intravenous fluid source. The passageway also passes through a rigid drip chamber, and a priming element that may be repeatedly compressed to urge fluid from the intravenous fluid source into the drip chamber and through the intravenous fluid line. The priming element includes a base and a priming membrane. The intravenous fluid line is mounted on the housing, such that the fluid passageway leads into the intravenous fluid line. The spike, the drip chamber, the base of the priming element and the receiving means all form an integral piece of rigid material. This embodiment may further include a valve chamber disposed in the housing, such that the fluid passageway leads into and out of the valve chamber through first and second mouths, with a valve membrane attached to the housing and disposed over the valve chamber so that the valve membrane may be urged to cover at least one of said first and second mouths, such that flow through the fluid passageway may be stopped. A cap having a hole defined therethrough may be disposed on the housing over the valve membrane, such that gas may be supplied through the hole to urge the valve membrane to cover at least one of said first and second mouths.

In an alternative embodiment, the invention may be used with first and second intravenous fluid sources and an intravenous fluid line. This embodiment includes a spike for connecting the device to the first intravenous fluid source. A fluid passageway passes through the spike. A puncture site connects the device to the second intravenous fluid source. This embodiment further includes an adjustable valve, which includes a flexible tube mounted so that fluid may pass from the fluid passageway in the spike, from the puncture site, and through the tube. The valve includes an actuator mounted with respect to the tube so that it may be urged to compress the tube. This embodiment also includes a drip chamber, through which the fluid may flow to the intravenous fluid line. The spike, the adjustable valve, and the drip chamber form an integral device. This embodiment may further include a one-way valve mounted below the spike and above the puncture site, so that intravenous fluid may flow from the fluid passageway through the one-way valve, and so that fluid from the second fluid source may flow to the intravenous fluid line, but may not flow through the fluid passageway in the spike. The adjustable valve in this embodiment may also include a rigid threaded seat disposed about the tube, a levered arm mounted on the threaded seat so that it may be urged to compress the tube, and a threaded nut engagedly and concentrically mounted on and about the seat, so that as the nut is turned it may urge the levered arm to compress the tube. The tube may be made of silicone.

In another embodiment, the invention may include a spike, having a fluid passageway disposed therethrough, for connecting the device to the intravenous fluid source, a one-way valve mounted below the spike, so that intravenous fluid may flow from the fluid passageway through the one-way valve, a puncture site mounted below the one-way valve, so that a second fluid may be introduced into the device and flow to the intravenous fluid line, but may not flow through the fluid passageway in the spike, and a drip chamber, through which the fluid may flow. The spike, the one-way valve, the puncture site, the drip chamber and the receiving means form an integral device.

In a further embodiment the invention includes a spike, a drip chamber, and an adjustable valve, which includes a flexible tube, a rigid threaded seat disposed about the tube, a levered actuator mounted on the threaded seat so that it may be urged to compress the tube, and a threaded nut engagedly and concentrically mounted on and about the seat, so that as the nut is turned it may urge the levered actuator to compress the tube.

The invention may be made of two substantially flat sections, such that when placed together, the two sections form a passageway, through which intravenous fluid may pass, the passageway having at least two expanded sections, one expanded section forming a drip chamber, and the second expanded section providing an area where filter material may be located.

In a preferred embodiment the length of the fluid passageway is more than twice the length of the housing, and the housing is made of a transparent thermoplastic material.

The invention may include a valve for automatically shutting off the flow of fluid. This valve includes a housing having a chamber disposed therein, a protrusion from the housing into the chamber, a fluid input through the housing into the chamber, a fluid output from the chamber through the protrusion and through the housing, and a membrane disposed on the housing, such that one side is exposed to the chamber and the second side is exposed to atmosphere. The membrane is disposed with respect to the mouth on the protrusion, such that the membrane may seal off the fluid output when the pressure of the fluid in the fluid input drops to a certain level. This valve may further include a cap having a hole defined therethrough, the cap being disposed on the housing over the membrane such that the second side may be exposed to atmosphere.

The invention may also include an adjustable valve for controlling the flow of fluid. This valve includes a flexible, multiple-lumen element disposed in the line such that fluid may pass through the multiple lumens, and an apparatus for squeezing the multiple-lumen element so as to constrict the multiple lumens. The multiple-lumen element may be made of silicone.

DESCRIPTION OF SPECIFIC EMBODIMENTS

Figure 2:
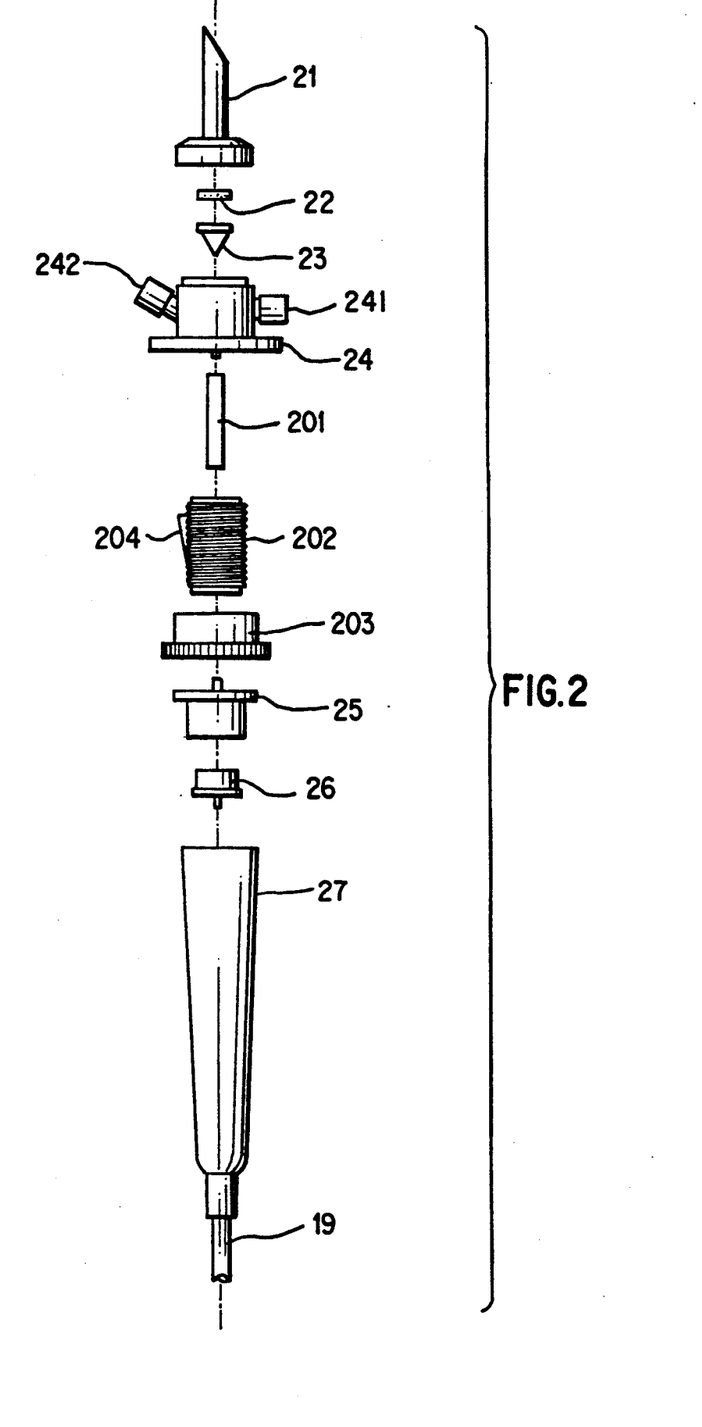
FIG. 2 is an exploded view of one embodiment of the invention.
Figure 3:
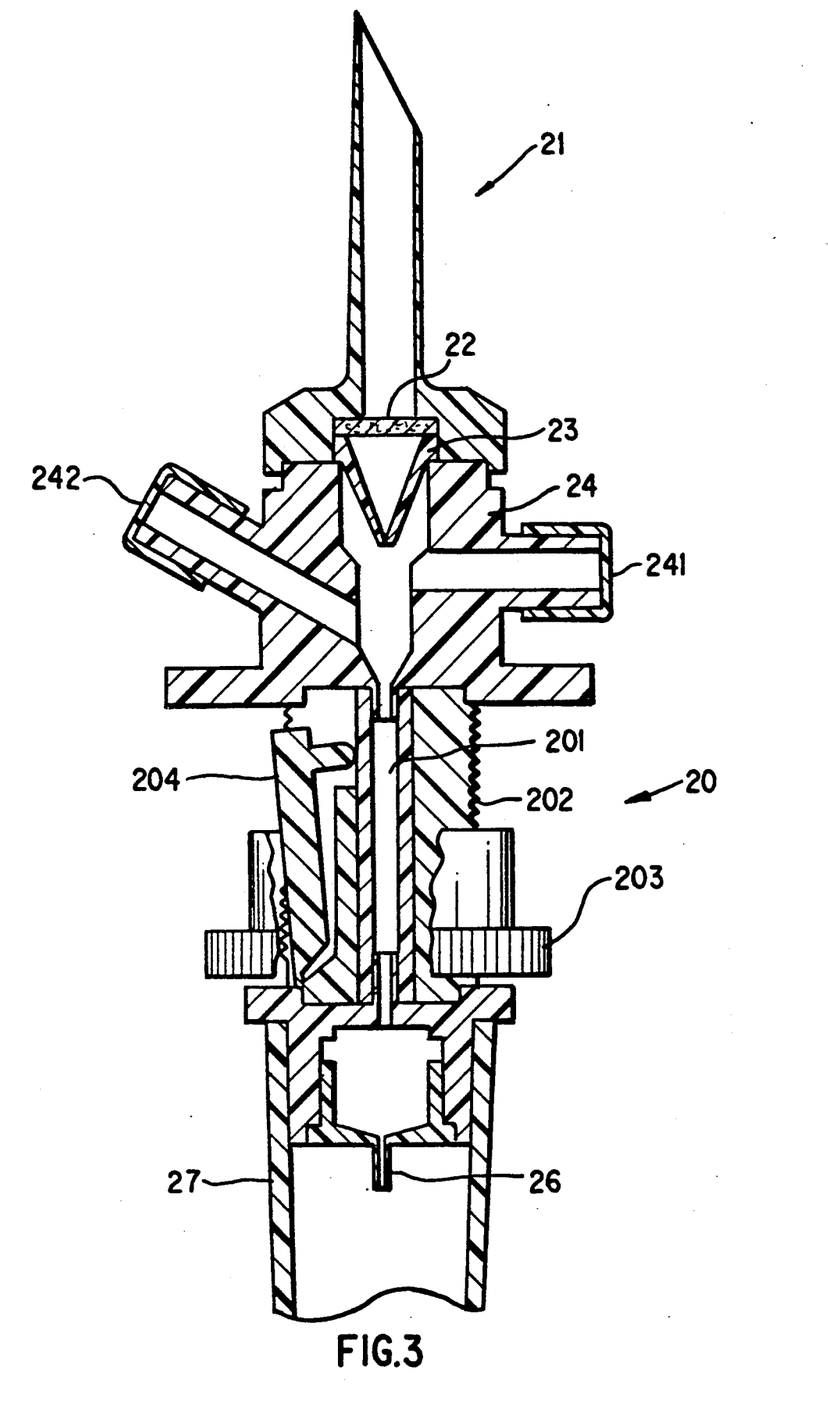
FIG. 3 is a cross-sectional view of the top portion of the device shown in FIG. 2.
Figure 4:
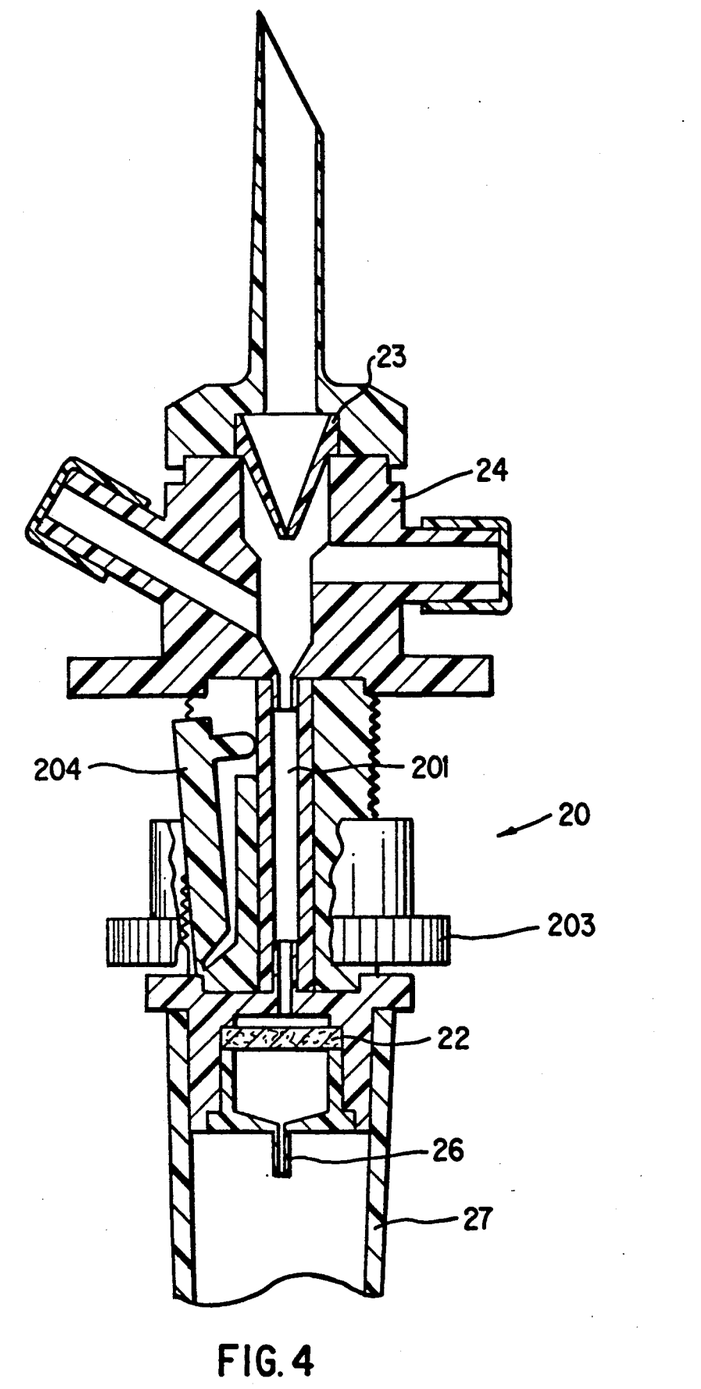
FIG. 4 is a cross-sectional view of the top portion of an alternative embodiment of the invention.

FIG. 2 shows how the components of one embodiment of the invention are assembled. FIG. 3 shows a cross section of the upper portion of such an embodiment. This structure includes a spike 21, a filter 22, a duckbill valve 23, puncture sites 241 and 242, an adjustable valve 20, and a drip chamber 27. The duckbill valve 23 is mounted above the cap 24 on which the puncture sites 241 and 242 are located. The puncture sites 241 and 242 are located above the adjustable valve 20. Various embodiments are possible, as shown, for example, in FIG. 4, wherein the filter 22 is put in a different position. Alternatively, other embodiments may dispense with one or more of the components or may include additional components.

The adjustable valve 20 includes a flexible tube 201 mounted so that fluid may pass from the spike 21, and from the puncture sites 241 and 242, and then through the tube 201. The valve 24 includes a levered actuator 204 mounted with respect to the tube 201 so that it may be urged to compress the tube 201. A rigid threaded seat 202 is disposed about the tube 201, and the levered actuator 204 is mounted on the threaded seat 202. A threaded nut 203 is engagedly and concentrically mounted on and about the seat 202, so that as the nut 203 is turned it may urge the levered actuator 204 to compress the tube 201.

Figure 5:
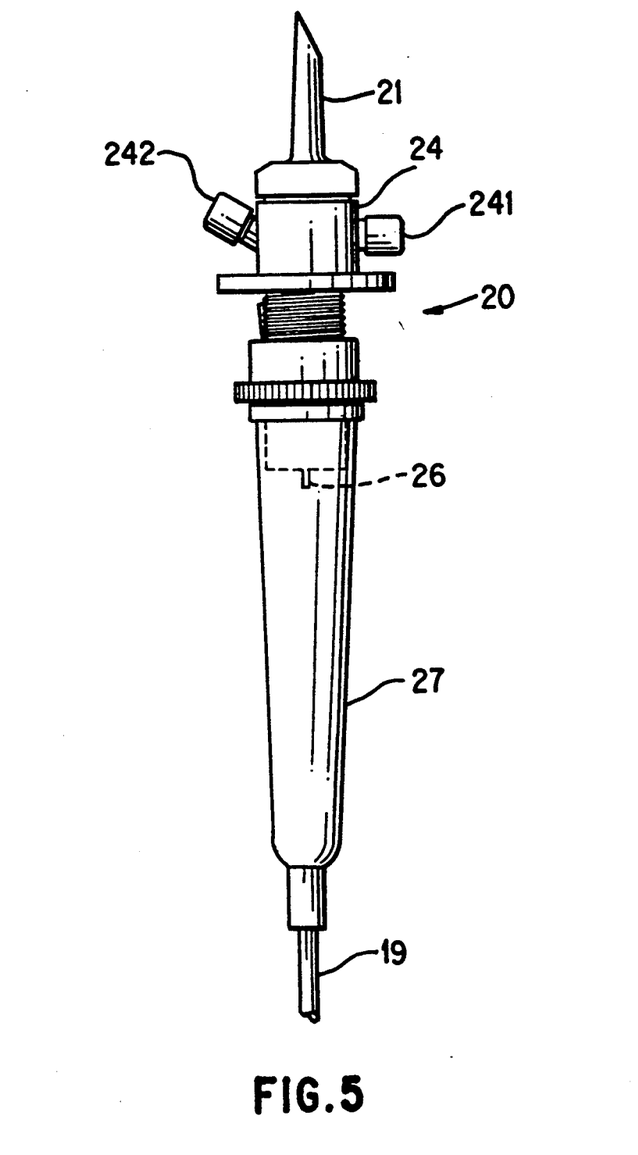
FIG. 5 shows the device of FIG. 2 assembled.

In addition to the compactness of the structure, the invention has several other advantages. Because all the components are connected directly to each other, it is easier and cheaper to manufacture than the conventional intravenous delivery systems, wherein the components must be cemented to the tubing 19. Also, in order to adjust the flow rate, a clamp 16 is not placed on the conventional intravenous tubing 19; instead silicone tubing 201, which provides much better properties for clamping, may be used in the adjustable valve 20. Thus, the adjustable valve 20 of the invention can be more effective in controlling the flow rate than the clamps used in the conventional systems. A further advantage is that a single system that counts drops in order to measure the flow rate may be used, instead of two such systems (one for the first source of intravenous fluid and a second for the second source of intravenous fluid) that are required to continuously measure flow in the conventional intravenous fluid delivery systems. This is possible because the puncture sites 241 and 242 are located above the canula 26 in the drip chamber 27, and therefore the fluid from both sources flow through the same canula 26. FIG. 5 shows an assembled embodiment.

Figure 6:
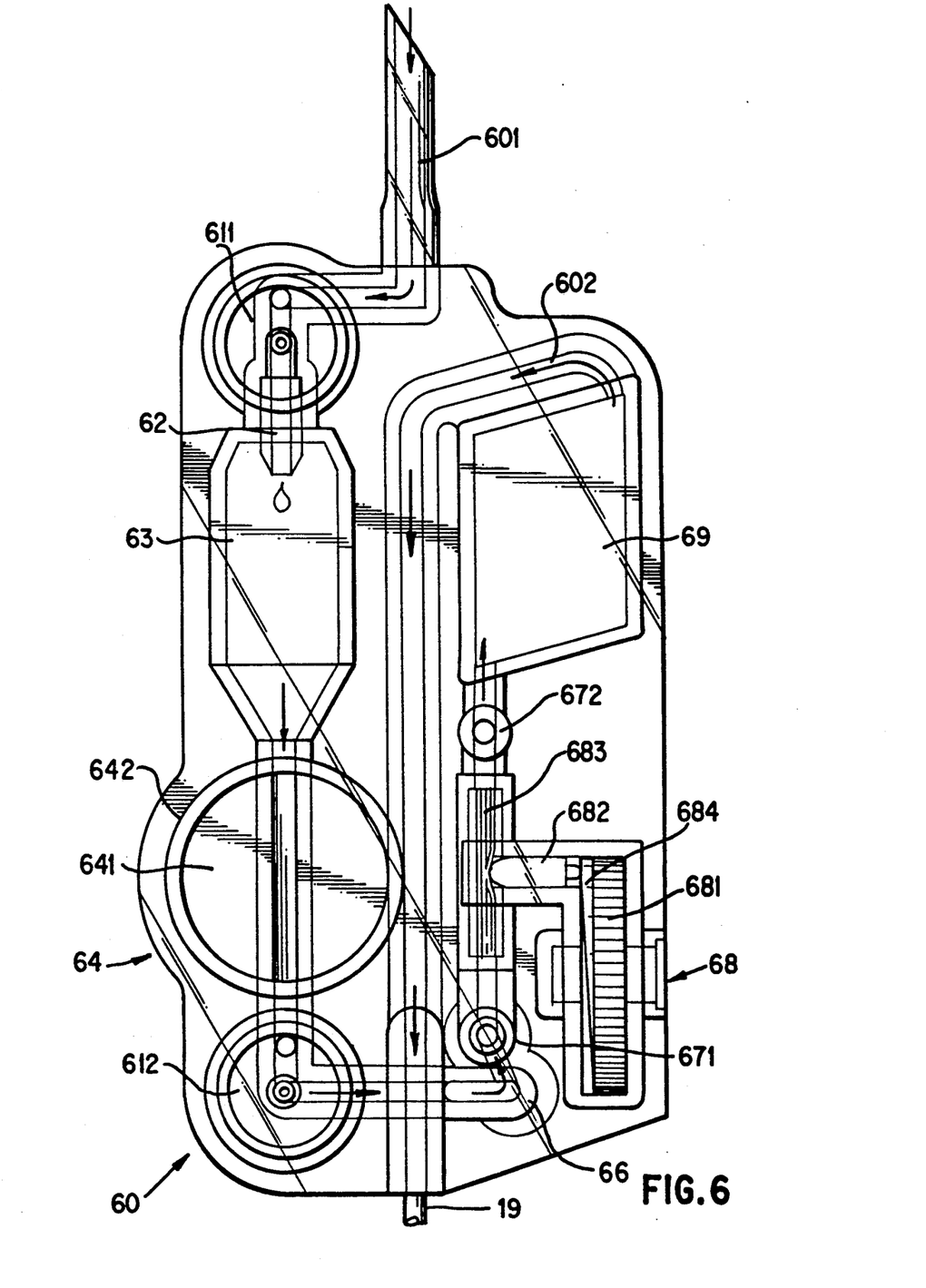
FIG. 6 shows a front view of another embodiment of the invention.
Figure 7:
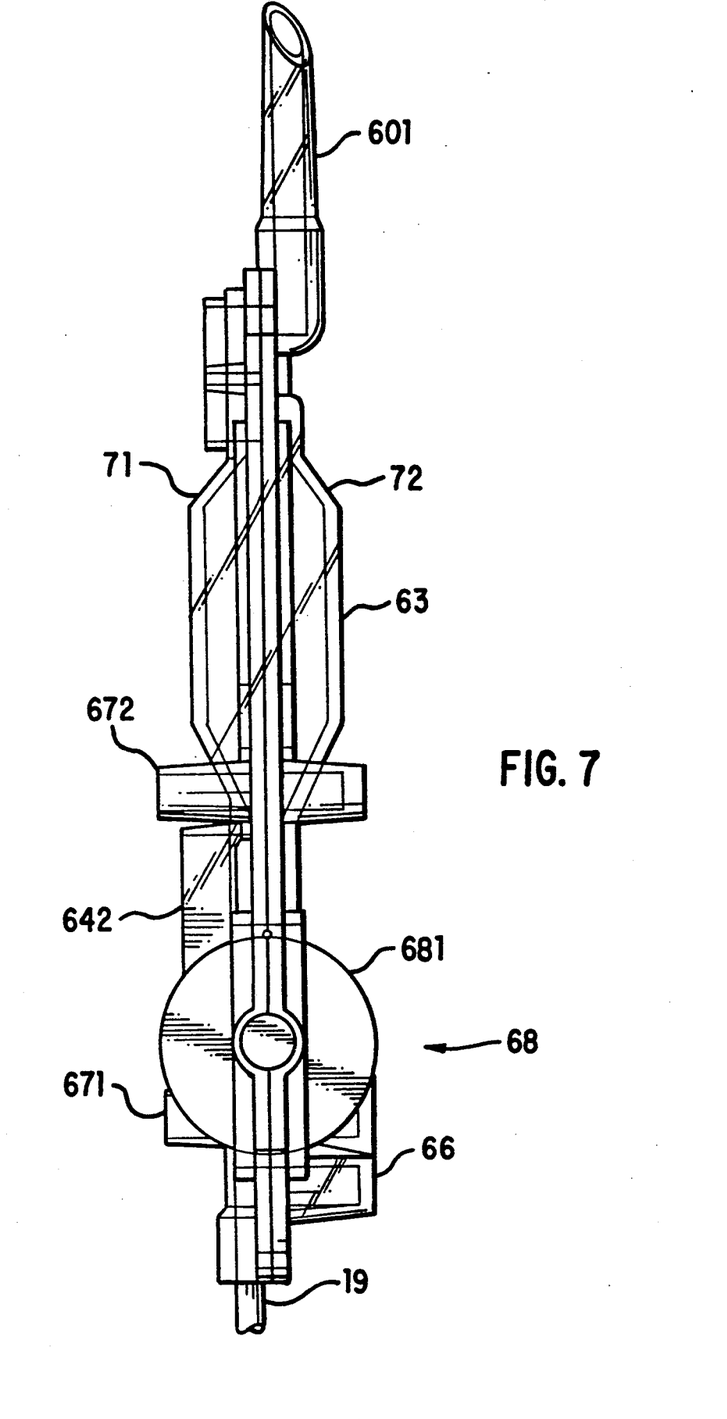
FIG. 7 shows a side view of the device shown in FIG. 6.

FIGS. 6 and 7 show an alternative embodiment of the invention. FIG. 6 shows a front view of the embodiment, and FIG. 7 shows a side view. A spike 601 is mounted at the top end of the housing 60. A fluid passageway 602 is disposed inside the housing 60 and the spike 601. The spike 601 is used to connect the device to a fluid source. Fluid from the fluid source passes through the fluid passageway 602 through the device and out of the device to the intravenous fluid line 19, which is connected to the device where the fluid passageway 602 exits the device. Disposed along the fluid passageway are two automatic shut-off valves 611 and 612, a drip chamber 63 located between the automatic shut-off valves 611 and 612, a one-way (duckbill) valve 66, two puncture sites 671 and 672, an adjustable control valve 68 located between the two puncture sites 671 and 672 and a filter 69. Other embodiments may not include all of these items, and the order that these items are disposed along the fluid passageway may be varied. It should be noted though that having the puncture sites 671 and 672 located downstream from the one-way valve 66 permits one to add a second fluid source in a manner similar to that shown in FIG. 1.

Figure 8:
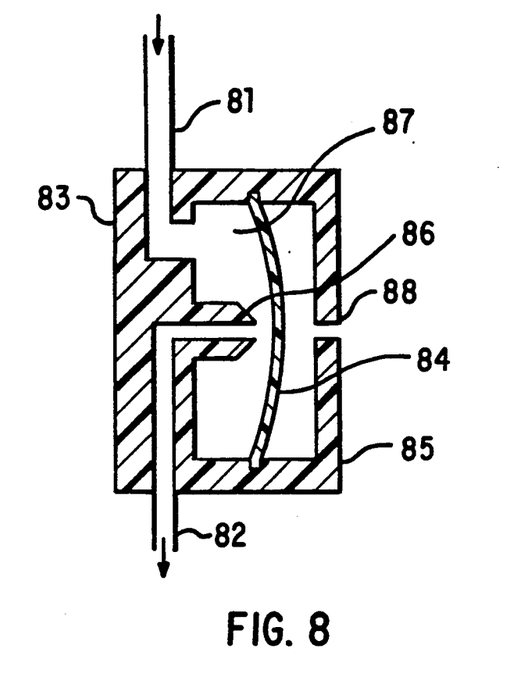
FIG. 8 shows a cross-section of an automatic shut-off valve.

The automatic shut-off valves 611 and 612 close when there is little or no fluid left upstream of the valve. Thus, when the fluid source empties, automatic shut-off valve 611 will close, thereby stopping the flow of fluid through the fluid passageway 602 and the intravenous line 19. This permits the replacement of the fluid source before air enters the intravenous line 19. Once air enters the intravenous line 19, usually a new line must be inserted into the patient. With prior art systems the amount of fluid remaining in the intravenous fluid bag or bottle would be closely watched, and the bottle or bag would be replaced before it emptied. With an automatic shut-off valve less attention would need to be paid to the amount of fluid remaining in the intravenous fluid source. FIG. 8 shows a cross-section of an embodiment of the automatic shut-off valve. Fluid enters the valve through an input 81 located at the top of the housing 83, and exits from the output 82 located at the bottom of the housing. The output 82 is connected, directly or indirectly, to an intravenous line. A chamber 87 is located in the housing. Fluid from the input 81 enters the chamber. Fluid exits from the chamber through a protrusion 86, from which the fluid flows to the output 82. A flexible membrane 84 is disposed across the chamber 87 opposite the protrusion 86. A cap 85 having an air hole 88 is mounted to the housing 83 so as to protect the membrane 84 from being accidentally torn. When there is fluid in the input 81 the head pressure of the fluid in the chamber 87 urges the membrane 84 away from the mouth of the protrusion 86. When the amount of fluid in or above the input 81, and the head pressure in the chamber 87, decrease enough, the suction caused by the fluid flowing out of the output 82 and through the intravenous line will cause the membrane 84 to seal over the mouth on the protrusion 86, thereby preventing any more fluid from exiting through the output 82. The tension of the membrane 84 and the position of the membrane with respect to the protrusion may be altered so as to control when the valve will automatically shut off.

The automatic shut-off valves 611 and 612 may double as control valves, shown as items A and B in FIG. 12 of co-pending U.S. patent application Ser. No. 345,387, referenced above. The membrane 84 can be urged against or away from the protrusion 86 so as to control whether fluid may flow through the valve, by placing the automatic shut-off valves against a control unit that supplies a gas through the automatic shut-off valve's air hole 88, so as to apply a pressure to the membrane 84.

The device shown in FIG. 6 also has a drip chamber 63. This drip chamber 63 may be made of the same relatively rigid material that the rest of the housing 60 is made of. Typically, drip chambers are made of a flexible, resilient material, so that the drip chamber may be repeatedly squeezed in order to prime the intravenous line. In order to prime the intravenous line 19 using the device shown in FIG. 6 a special primer 64 is used. The primer 64 consists of a flexible, resilient material 641 that forms an expanded area in the fluid passageway and that may be repeatedly squeezed in order to prime the intravenous line. It is preferable that this flexible, resilient material 641 protrude away from the surface of the housing 60 in order to make it easier to squeeze. A protective rigid annulus 642 can be mounted to the housing 60 around the flexible material 641 of the primer 64. The primer 64 can double as the pressure conduction chamber shown as item 2 in FIG. 12 of co-pending U.S. patent application Ser. No. 345,387, discussed above. Thus, the primer 64 and the two automatic shut-off valves 611 and 612 can function like the disposable system shown as item 124 in FIG. 12 of this co-pending application, simply by using the device with an appropriate central unit (similar to item 125 of FIG. 12 of this co-pending application) that can apply gas pressure to the membranes of the automatic shut-off valves 611 and 612 and the flexible, resilient material of the primer 64.

Thus, the device shown in FIG. 6 can be used by itself, or it can be used with an appropriate control unit so as to measure the flow rate of the intravenous fluid flowing through the device, in a manner described in co-pending application Serial No. 345,387. In order to properly work in this manner (wherein Boyle's Law is used to measure the flow rate), the primer 64, which is doubling as a pressure conduction chamber, must be completely filled with liquid, and must not be in pressure communication with any other chamber that may have air in it. Thus, the primer 64 may either be isolated from the drip chamber 63 by placing another valve between the primer 64 and the drip chamber 63, or the drip chamber 63 can be completely filled with liquid.

The device can also be used with a system that measures the flow rate by counting the number of drops that fall in the drip chamber.

Figure 9A:
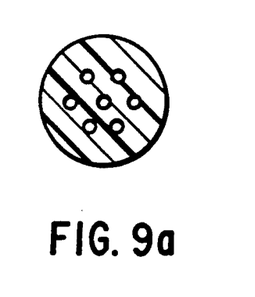
FIG. 9a shows a cross section of a multi-lumen tube.
Figure 9B:
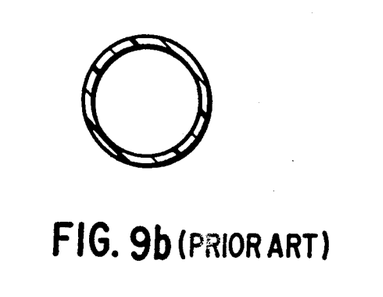
FIG. 9b shows a cross-section of a typical tube.

The adjustable valve 68 shown in FIG. 6 includes a multi-lumen tube 683, preferably made of silicone, a finger 682 and a rotatably mounted cam 681 having a helical ramp 684 thereon. When the cam 681 is turned, the helical ramp 684 urges the finger 682 against the multi-lumen tube 683, thereby restricting the flow through the tube 683. If the cam 681 is turned enough, the helical ramp 684 forces the finger 682 far enough to the left that flow through the tube 683 is completely stopped. A cross-section of the multi-lumen tube is shown in FIG. 9a. The tube has seven passages, through which fluid may pass. By using a multi-lumen tube, shown in cross-section in FIG. 9b, one can control the fluid flow with greater precision. When a conventional intravenous tube is compressed, although it does tend to flatten, there is very little effect on the flow rate until the tube it is almost completely shut; at that point the flow rate drops off very quickly. When compressing a multi-lumen tube, the flow rate decreases more gradually over a wider range of compression. It is believed that the individual lumens are squeezed shut at different points during the compression. Thus, under slight compression only one lumen may be almost completely shut, and under greater compression two lumens may be almost completely shut, and under still greater compression three lumens may be shut, etc. The multi-lumen tube, therefore, provides greater control at intermediate flow rates.

After passing through the automatic shut-off valves 611 and 612, the drip chamber 63 and the primer 64, the fluid passageway 602 passes through the one-way valve 66 and then heads up through the control valve 68 and the filter 69 before coming back down to connect with the intravenous tube 19. By having the fluid passageway 602 snake back and forth across the length of the device, the device is sturdier than if it were constructed with a straight passageway. If the passageway did not have a bend or two, the resulting device would be relatively long and narrow, and more prone to breaking. By bending the passageway 602 several times, the device is sturdier and more compact. In the embodiment shown in FIG. 6 the fluid passageway traverses the length of the device nearly three times.

The device shown in FIG. 6 is preferably made of a clear thermoplastic material. Making the device transparent assists the user in making sure the intravenous fluid is properly flowing through the device. The device can be made from two relatively flat halves 71 and 72 as shown in FIG. 7. The fluid passageway can be formed by placing a groove on either one, or both, of the two halves. During assembly, the drip chamber's canula 62, the primer's flexible material 641, the one-way valve 66, the control valve's cam 681, finger 682 and tube 683, and the filter material 69, can be placed on one of the halves, and the second half can be attached to the first, securing these items in place. This provides a simple, efficient and inexpensive method for assembling a complete intravenous fluid delivery system. In order to assist assembly, the cam wheel 681 and the finger 682 may be initially attached to each other; after they have been inserted into one of the halves of the device, the finger 682 can be broken off the cam wheel 681, when the device is assembled. As noted above, prior art systems connected the various components together by tubing. The cementing of each component to the tubing is a relatively slow procedure. By placing all the components in a single housing that can be assembled by merely attaching two halves together one can produce a complete intravenous delivery systems much more cheaply.

What is claimed is:

1. An integral intravenous fluid delivery device for use between an intravenous fluid source and an intravenous fluid line in fluid communication with a patient, the device comprising:
   a housing including a fluid passageway, the passageway having a portion through which fluid normally flows against gravity;
   a spike for connecting the rigid housing directly to the intravenous fluid source, another portion of the fluid passageway being disposed in the spike;
   a rigid drip chamber, the fluid passageway passing through the drip chamber;
   repeatedly compressible priming means for urging fluid from the intravenous fluid source into the drip chamber and through the intravenous fluid line, the priming means including a rigid portion and a flexible portion, including a priming membrane, the priming means being in fluid communicating with the fluid passageway; and
   means, mounted on the housing, for receiving the intravenous fluid line, such that the fluid passageway leads into the intravenous fluid line;
   wherein the spike, the drip chamber, the rigid portion of the priming means and the receiving means all form an integral piece of rigid material; and further including
   a valve chamber disposed in the housing, such that the fluid passageway leads into and out of the valve chamber through first and second mouths; and
   a valve membrane attached to the housing and disposed over the valve chamber so that the valve membrane may be urged to cover at least one of said first and second mouths, such that flow through the fluid passageway may be stopped; and further including
   a cap having a hold defined therethrough, the cap being disposed on the housing over the valve membrane, such that gas may be supplied through the hole to urge the valve membrane to cover at least one of said first and second mouths.

2. An integral intravenous fluid delivery device for use between an intravenous fluid source and an intravenous fluid line in fluid communication with a patient, the device comprising:
   a housing including a fluid passageway, the passageway having a portion through which fluid normally flows against gravity;
   a spike for connecting the rigid housing directly to the intravenous fluid source, another portion of the fluid passageway being disposed in the spike;
   a rigid drip chamber, the fluid passageway passing through the drip chamber;
   repeatedly compressible priming means for urging fluid from the intravenous fluid source into the drip chamber and through the intravenous fluid line, the priming means including a rigid portion and a flexible portion, including a priming membrane, the priming means being in fluid communication with the fluid passageway; and
   means, mounted on the housing, for receiving the intravenous fluid line, such that the fluid passageway leads into the intravenous fluid line;
   wherein the spike, the drip chamber, the rigid portion of the priming means and the receiving means all form an integral piece of rigid material; further including
   a valve chamber disposed in the housing, such that the fluid passageway leads into and out of the valve chamber through first and second mouths; and
   a valve membrane attached to the housing and disposed over the valve chamber so that the valve membrane may be urged to cover at least one of said first and second mouths, such that flow through the fluid passageway may be stopped; and, further including
   a protrusion located in the valve chamber opposite the valve membrane, the fluid passageway passing through the protrusion, and at least one of said first and second mouths being located on the protrusion.

3. An integral intravenous fluid delivery device according to claim 1, further including
   a protrusion located in the valve chamber opposite the valve membrane, the fluid passageway passing through the protrusion, and at least one of said first and second mouths being located on the protrusion.

4. An integral intravenous fluid delivery device according to claim 2, wherein the first mouth is a fluid input to the chamber, and the second mouth is mounted on the protrusion and is a fluid output from the chamber;
   wherein the membrane, having first and second sides, is disposed on the housing, such that the first side is exposed to the chamber and the second side is exposed to atmosphere; and
   wherein the membrane is disposed with respect to the second mouth on the protrusion, such that the membrane may seal off the second mouth when the pressure of the fluid in the first mouth drops to a certain level.

5. An integral intravenous fluid delivery device according to claim 3, wherein the first mouth is a fluid input to the chamber, and the second mouth is mounted on the protrusion and is a fluid output rom the chamber;

wherein the membrane, having first and second sides, is disposed on the housing, such that the first side is exposed to the chamber and the second side is exposed to atmosphere; and wherein the membrane is disposed with respect to the second mouth on the protrusion; such that the membrane may seal off the second mouth when the pressure of the fluid in the first mouth drops to a certain level.

6. An integral intravenous fluid delivery device for use between an intravenous fluid source and an intravenous fluid line in fluid communication with a patient, the device comprising:

a housing including a fluid passageway;

a spike for connecting the rigid housing directly to the intravenous fluid source, a portion of the fluid passageway being disposed in the spike;

a rigid drip chamber, the fluid passageway passing through the drip chamber;

repeatedly compressible priming means for urging fluid from the intravenous fluid source into the drip chamber and through the intravenous fluid line, the priming means including a rigid portion and a flexible portion, including a priming membrane, the priming means being in fluid communication with the fluid passageway; and means, mounted on the housing, for receiving the intravenous fluid line, such that the fluid passageway leads into the intravenous fluid line;

wherein the spike, the drip chamber, the rigid portion of the priming means and the receiving means all form an integral piece or rigid material; further including a valve chamber disposed in the housing, such that the fluid passageway leads into and out of the valve chamber through first and second mouths; and a valve membrane attached to the housing and disposed over the valve chamber so that the valve membrane may be urged to cover at least one of said first and second mouths, such that flow through the fluid passageway may be stopped; and further including a protrusion located in the valve chamber opposite the valve membrane, the fluid passageway passing through the protrusion, and at least one of said first and second mouths being located on the protrusion.

7. An integral intravenous fluid delivery according to claim 6, wherein the first mouth is a fluid input to the chamber, and the second mouth is mounted on the protrusion and is a fluid output from the chamber;

wherein the membrane, having first and second sides, is disposed on the housing, such that the first side is exposed to the chamber and the second side is exposed to atmosphere; and wherein the membrane is disposed with respect to the second mouth on the protrusion, such that the membrane may seal off the second mouth when the pressure of the fluid in the first mouth drops to a certain level.

8. An integral intravenous fluid delivery device for use between an intravenous fluid source and an intravenous fluid line in fluid communication with a patient, the device comprising:

a housing including a fluid passageway;

a spike for connecting the rigid housing directly to the intravenous fluid source, a portion of the fluid passageway being disposed in the spike;

a rigid drip chamber, the fluid passageway passing through the drip chamber;

repeatedly compressible priming means for urging fluid from the intravenous fluid source into the drip chamber and through the intravenous fluid line, the priming means including a rigid portion and a flexible portion, including a priming membrane, the priming means being in fluid communication with the fluid passageway; and means, mounted on the housing, for receiving the intravenous fluid line, such that the fluid passageway leads into the intravenous fluid line;

wherein the spike, the drip chamber, the rigid portion of the priming means and the receiving means all form an integral piece of rigid material; and further including a valve chamber disposed in the housing, such that the fluid passageway leads into and out of the valve chamber through first and second mouths; and a valve membrane attached to the housing and disposed over the valve chamber so that the valve membrane may be urged to cover at least one of said first and second mouths, such that flow through the fluid passageway may be stopped; and further including a cap having a hole defined therethrough, the cap being disposed on the housing over the valve membrane, such that gas may be supplied through the hole to urge the valve membrane to cover at least one of said first and second mouths.

9. An integral intravenous fluid delivery device according to claim 8, further including a protrusion located in the valve chamber opposite the valve membrane, the fluid passageway passing through the protrusion, and at least one of said first and second mouths being located on the protrusion.

10. An integral intravenous fluid delivery device according to claim 9, wherein the first mouth is a fluid input to the chamber, and the second mouth is mounted on the protrusion and is a fluid output from the chamber;

wherein the membrane, having first and second sides, is disposed on the housing, such that the first side is exposed to the chamber and the second side is exposed to atmosphere; and wherein the membrane is disposed with respect to the second mouth on the protrusion, such that the membrane may seal off the second mouth when the pressure of the fluid in the first mouth drops to a certain level.

11. An integral intravenous fluid delivery device for use between an intravenous fluid source and an intravenous fluid line in fluid communication with a patient, the device comprising;

a housing including a fluid passageway, the passageway having an inlet and an outlet, and passing through a spike, mounted on the housing, for connecting the housing and the passageway's inlet directly to the intravenous fluid source;

means, located at the passageway's outlet, for receiving the intravenous fluid line, such that the passageway leads into the intravenous fluid line;

a drip chamber, located between the spike and the line receiving means;

first and second valves located between the spike and the receiving means, one of said first and second valves including a valve chamber defined by the housing and a valve-chamber flexible membrane, such that the fluid passageway leads into and out of the valve chamber through first and second valve-chamber mouths, and at least one of said first and second valve-chamber mouths being located on a protrusion located in the valve chamber opposite the valve membrane; and a pumping chamber defined by the housing and a pumping-chamber flexible membrane, such that the fluid passageway leads into and out of the pumping chamber through first and second pumping-chamber mouths, the pumping chamber being located between the first and second valves.

12. An integral intravenous fluid delivery device according to claim 11, wherein the first mouth of the valve chamber is a fluid input to the chamber, and the second mouth of the valve chamber is mounted on the protrusion and is a fluid output from the chamber;

wherein the valve-chamber membrane, having first and second sides, is disposed on the housing, such that the first side is exposed to the chamber and the second side is exposed to atmosphere; and wherein the membrane is disposed with respect to the second mouth on the protrusion, such that the membrane may seal off the second mouth when the pressure of the fluid in the first mouth drops to a certain level.

13. An integral intravenous fluid delivery device for use between an intravenous fluid source and an intravenous fluid line in fluid communication with a patient, the device comprising:

a housing including a fluid passageway, the passageway having an inlet and an outlet, and passing through a spike, mounted on the housing, for connecting the housing and the passageway's inlet directly to the intravenous fluid source;

means, located at the passageway's outlet, for receiving the intravenous fluid line, such that the passageway leads into the intravenous fluid line;

a drip chamber, located between the spike and the line receiving means;

first and second valve chambers located between the spike and the receiving means, each of the first and second valve chambers being defined by the housing and a valve-chamber flexible membrane, such that the fluid passageway leads into and out of each valve chamber through first and second valve-chamber mouths, and at least one of said first and second valve-chamber mouths being located on a protrusion located in the valve chamber opposite the valve membrane; and a pumping chamber defined by the housing and a pumping-chamber flexible membrane, such that the fluid passageway leads into and out of the pumping chamber through first and second pumping-chamber mouths, the pumping chamber being located between the first and second valve chambers.

14. An integral intravenous fluid delivery device according to claim 13, wherein the first mouth of the first valve chamber is a fluid input to the chamber, and the second mouth of the first valve chamber is mounted on the protrusion and is a fluid output from the chamber;

wherein the first valve-chamber membrane, having first and second sides, is disposed on the housing, such that the first side is exposed to the chamber and the second side is exposed to atmosphere; and wherein the membrane is disposed with respect to the second mouth on the protrusion, such that the membrane may seal off the second mouth when the pressure of the fluid in the first mouth drops to a certain level.

* * * * *